(12) United States Patent
Sudo et al.

(10) Patent No.: US 7,927,315 B2
(45) Date of Patent: Apr. 19, 2011

(54) PISTON FOR A SYRINGE AND A PREFILLED SYRINGE USING THE SAME

(75) Inventors: Masamichi Sudo, Tokyo (JP); Morihiro Sudo, Tokyo (JP)

(73) Assignee: Daikyo Seiko, Ltd., Tokyo (JP)

( * ) Notice: Subject to any disclaimer, the term of this patent is extended or adjusted under 35 U.S.C. 154(b) by 1461 days.

(21) Appl. No.: 10/947,258

(22) Filed: Sep. 23, 2004

(65) Prior Publication Data

US 2005/0137533 A1 Jun. 23, 2005

(30) Foreign Application Priority Data

Dec. 17, 2003 (JP) ................................. 2003-419685

(51) Int. Cl.
*A61M 5/315* (2006.01)
(52) U.S. Cl. ...................................................... 604/218
(58) Field of Classification Search .................. 604/218, 604/187, 230, 110, 222, 15, 18, 38
See application file for complete search history.

(56) References Cited

U.S. PATENT DOCUMENTS

| | | | | |
|---|---|---|---|---|
| 422,437 A * | 3/1890 | Otto | ............................... | 604/219 |
| 2,578,394 A * | 12/1951 | Blackman | ...................... | 604/194 |
| 2,895,773 A * | 7/1959 | McConnaughey | ............... | 92/245 |
| 3,050,059 A * | 8/1962 | Wall et al. | ..................... | 604/222 |
| 3,354,882 A * | 11/1967 | Coanda | .......................... | 604/222 |
| 3,766,918 A * | 10/1973 | Kessel | ........................... | 604/125 |
| 3,998,224 A * | 12/1976 | Chiquiar-Arias | ............. | 604/110 |
| 4,303,070 A * | 12/1981 | Ichikawa et al. | ............... | 604/222 |
| 4,363,329 A * | 12/1982 | Raitto | ............................ | 600/578 |
| 4,381,779 A * | 5/1983 | Margulies | ...................... | 604/202 |
| 4,405,249 A * | 9/1983 | Scales | ............................... | 606/93 |
| 4,543,093 A * | 9/1985 | Christinger | ................... | 604/228 |
| 4,883,471 A * | 11/1989 | Braginetz et al. | .............. | 604/195 |
| 4,946,441 A * | 8/1990 | Laderoute | ...................... | 604/110 |
| 4,997,423 A * | 3/1991 | Okuda et al. | .................. | 604/230 |
| 5,009,646 A * | 4/1991 | Sudo et al. | ..................... | 604/230 |
| 5,037,382 A * | 8/1991 | Kvorning et al. | ............. | 604/220 |
| 5,062,833 A * | 11/1991 | Perler | ............................ | 604/110 |
| 5,085,638 A * | 2/1992 | Farbstein et al. | ............. | 604/110 |
| 5,085,640 A * | 2/1992 | Gibbs | ............................ | 604/110 |
| 5,194,335 A * | 3/1993 | Effenberger et al. | ......... | 428/421 |
| 5,201,709 A * | 4/1993 | Capra et al. | ................... | 604/110 |
| 5,290,235 A * | 3/1994 | Polyblank et al. | ............ | 604/110 |
| 5,354,286 A * | 10/1994 | Mesa et al. | ..................... | 604/230 |
| 5,413,563 A * | 5/1995 | Basile et al. | ................... | 604/218 |
| 5,554,125 A * | 9/1996 | Reynolds | ....................... | 604/187 |
| 5,562,623 A * | 10/1996 | Shonfeld et al. | .............. | 604/110 |
| 5,667,495 A * | 9/1997 | Bitdinger et al. | ............. | 604/220 |
| 5,782,815 A * | 7/1998 | Yanai et al. | ................... | 604/218 |
| 5,823,373 A * | 10/1998 | Sudo et al. | ..................... | 215/249 |
| 5,865,227 A * | 2/1999 | Carilli | ........................... | 141/328 |

(Continued)

FOREIGN PATENT DOCUMENTS

JP 8-308688 11/1996

(Continued)

*Primary Examiner* — Kevin C. Sirmons
*Assistant Examiner* — Michael J Anderson
(74) *Attorney, Agent, or Firm* — Wenderoth, Lind & Ponack, L.L.P.

(57) ABSTRACT

A sealing stopper or piston for a syringe which includes a skirt part that is capable of serving as a backstop device, and a prefilled syringe using the same. The skirt part provides a backstop function, i.e. it prevents reverse movement of the piston, without increasing production costs.

20 Claims, 4 Drawing Sheets

U.S. PATENT DOCUMENTS

| | | | | |
|---|---|---|---|---|
| 5,873,861 A * | 2/1999 | Hitchins et al. | | 604/218 |
| 5,891,052 A * | 4/1999 | Simmons | | 600/573 |
| 5,944,694 A * | 8/1999 | Hitchins et al. | | 604/154 |
| 5,951,527 A * | 9/1999 | Sudo | | 604/218 |
| 5,994,465 A * | 11/1999 | Sudo et al. | | 525/105 |
| 6,004,300 A * | 12/1999 | Butcher et al. | | 604/222 |
| 6,007,520 A * | 12/1999 | Sudo | | 604/181 |
| 6,017,330 A * | 1/2000 | Hitchins et al. | | 604/218 |
| 6,042,770 A * | 3/2000 | Sudo et al. | | 264/248 |
| 6,053,895 A * | 4/2000 | Kolberg et al. | | 604/218 |
| 6,090,081 A * | 7/2000 | Sudo et al. | | 604/230 |
| 6,120,479 A * | 9/2000 | Campbell et al. | | 604/110 |
| 6,129,712 A * | 10/2000 | Sudo et al. | | 604/218 |
| 6,142,977 A * | 11/2000 | Kolberg et al. | | 604/218 |
| 6,171,670 B1 * | 1/2001 | Sudo et al. | | 428/35.7 |
| 6,283,941 B1 * | 9/2001 | Schoenfeld et al. | | 604/110 |
| 6,322,535 B1 * | 11/2001 | Hitchins et al. | | 604/154 |
| 6,344,034 B1 * | 2/2002 | Sudo et al. | | 604/263 |
| 6,368,300 B1 * | 4/2002 | Fallon et al. | | 604/59 |
| 6,494,863 B1 * | 12/2002 | Shaw et al. | | 604/110 |
| 6,524,282 B1 * | 2/2003 | Sudo et al. | | 604/263 |
| 6,756,008 B2 * | 6/2004 | Sudo | | 264/328.1 |
| 6,796,217 B2 * | 9/2004 | Horita et al. | | 92/240 |
| 6,984,222 B1 * | 1/2006 | Hitchins et al. | | 604/218 |
| 7,063,684 B2 * | 6/2006 | Moberg | | 604/155 |
| 7,111,848 B2 * | 9/2006 | Tachikawa et al. | | 277/535 |
| 7,141,042 B2 * | 11/2006 | Lubrecht | | 604/230 |
| 7,195,609 B2 * | 3/2007 | Huegli | | 604/67 |
| 7,214,214 B2 * | 5/2007 | Sudo et al. | | 604/263 |
| 2002/0003122 A1 * | 1/2002 | Sudo | | 215/247 |
| 2002/0022809 A1 * | 2/2002 | Sudo et al. | | 604/263 |
| 2002/0048669 A1 * | 4/2002 | Sudo et al. | | 428/212 |
| 2002/0128627 A1 * | 9/2002 | Sudo | | 604/403 |
| 2002/0173753 A1 * | 11/2002 | Caizza et al. | | 604/241 |
| 2003/0032928 A1 * | 2/2003 | Sudo et al. | | 604/225 |
| 2003/0094429 A1 * | 5/2003 | Sudo et al. | | 215/316 |
| 2003/0205838 A1 * | 11/2003 | Sudo et al. | | 264/161 |
| 2006/0054586 A1 * | 3/2006 | Sudo et al. | | 215/355 |
| 2006/0178643 A1 * | 8/2006 | Sudo et al. | | 604/230 |

FOREIGN PATENT DOCUMENTS

| | | |
|---|---|---|
| JP | 2914826 | 4/1999 |
| JP | 3387775 | 1/2003 |
| WO | 01/64266 | 9/2001 |

* cited by examiner

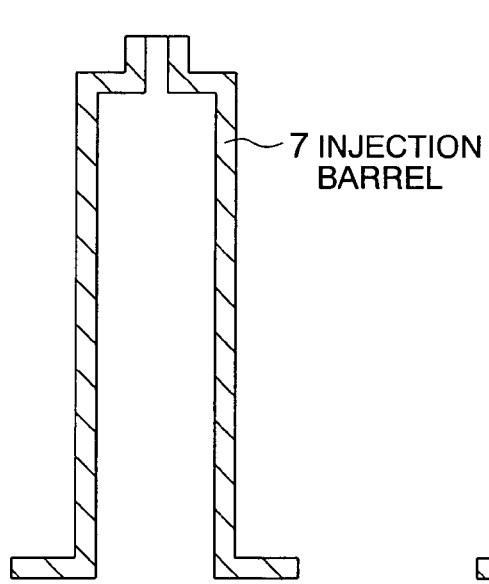
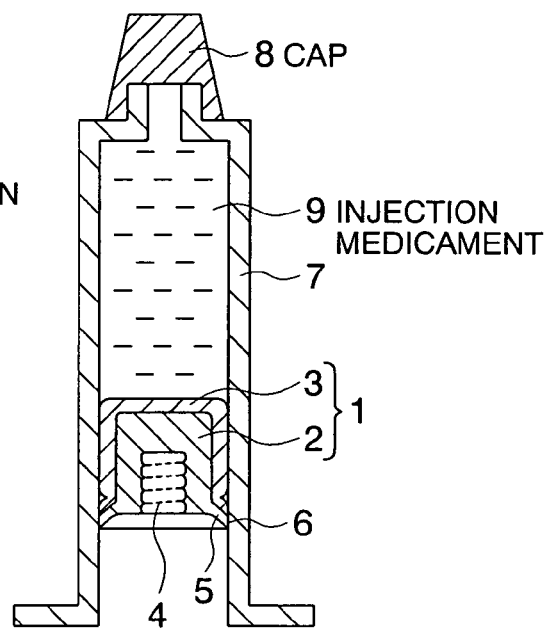
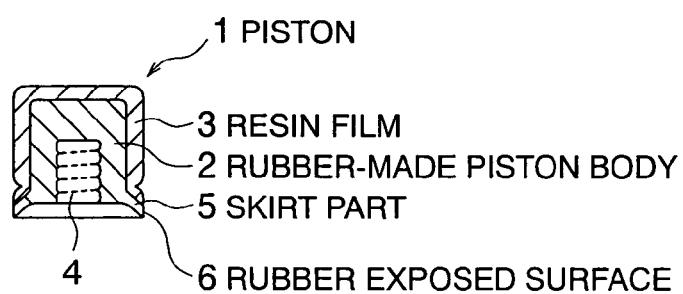
FIG. 1B   FIG. 1C
FIG. 1A

PISTON FOR A SYRINGE AND A PREFILLED SYRINGE USING THE SAME

BACKGROUND OF THE INVENTION

1. Field of the Invention

This invention relates to a sealing stopper or piston for a syringe provided with a backstop function and to a prefilled syringe using the same.

2. Description of the Prior Art

As a method of feeding an injection agent as one agent form of a medicament to a medical scene, there is the system of a prefilled syringe, in which the injection agent is previously prepared (charged) in a syringe-cum-container, transported and stored with the end part thereof sealed by a piston. The front end of the injection barrel is fitted with an injection needle or administration device during administration, and the piston is forcibly thrust toward the front end and slidably moved in the injection barrel so as to cause the injection agent to flow out of the injection needle side, as depicted in JP-B2-3387775. This method has lately been applied to various uses, because of the advantages that (1) operation is very simple, (2) administration can be accomplished with the correct administered quantity and without misuse of a medicament agent even in an emergency and (3) there is no necessity of transferring a liquid medicament, which results in easy avoidance of contamination with micro-organisms, as well as obtaining high sanitary properties. The prefilled syringe is of a disposal type such that the prefilled syringe, once used, should be abandoned due to sanitary problems such as infectious diseases.

Since the above described syringe, once used, is ordinarily abandoned in a usable state if refilled with a liquid medicament, there is a possibility that the abandoned syringe can be reused for a criminal act such as injection of stimulants, or can be misused again in a medical scene. In order to completely prevent these dangers, it is desirable to provide such a mechanism such that once used, the syringe is no longer reusable.

As a syringe provided with such a mechanism, for example, there is a structure in which a plunger threaded with a piston has a reuse-preventive projection which is engaged with a recess of an injection barrel when the plunger is pushed, so that the plunger cannot be withdrawn (called a backstop), as shown in WO 01/64266 A1. However, the mechanism of this syringe is so complicated that its production cost is considerably increased.

SUMMARY OF THE INVENTION

It is an object of the present invention to provide a prefilled syringe having a backstop function without increasing the production cost thereof, whereby the disadvantages of the prior art can be overcome.

It is another object of the present invention to provide a sealing stopper or a piston for a syringe, having a reuse preventive backstop mechanism, in an economical manner.

These objects can be achieved by a piston for a syringe for sealing an injection barrel filled with a medicament comprising a skirt part capable of serving as a backstop device.

BRIEF DESCRIPTION OF THE DRAWINGS

The accompanying drawings are to illustrate the principle and merits of the present invention in detail.

FIGS. 1A-1C are cross-sectional views of one embodiment of a piston for a syringe and a prefilled syringe using the same according to the present invention, FIG. 1A shows a piston or sealing stopper, FIG. 1B shows an injection barrel and FIG. 1C shows a prefilled syringe.

DETAILED DESCRIPTION OF THE INVENTION

Figure 2:
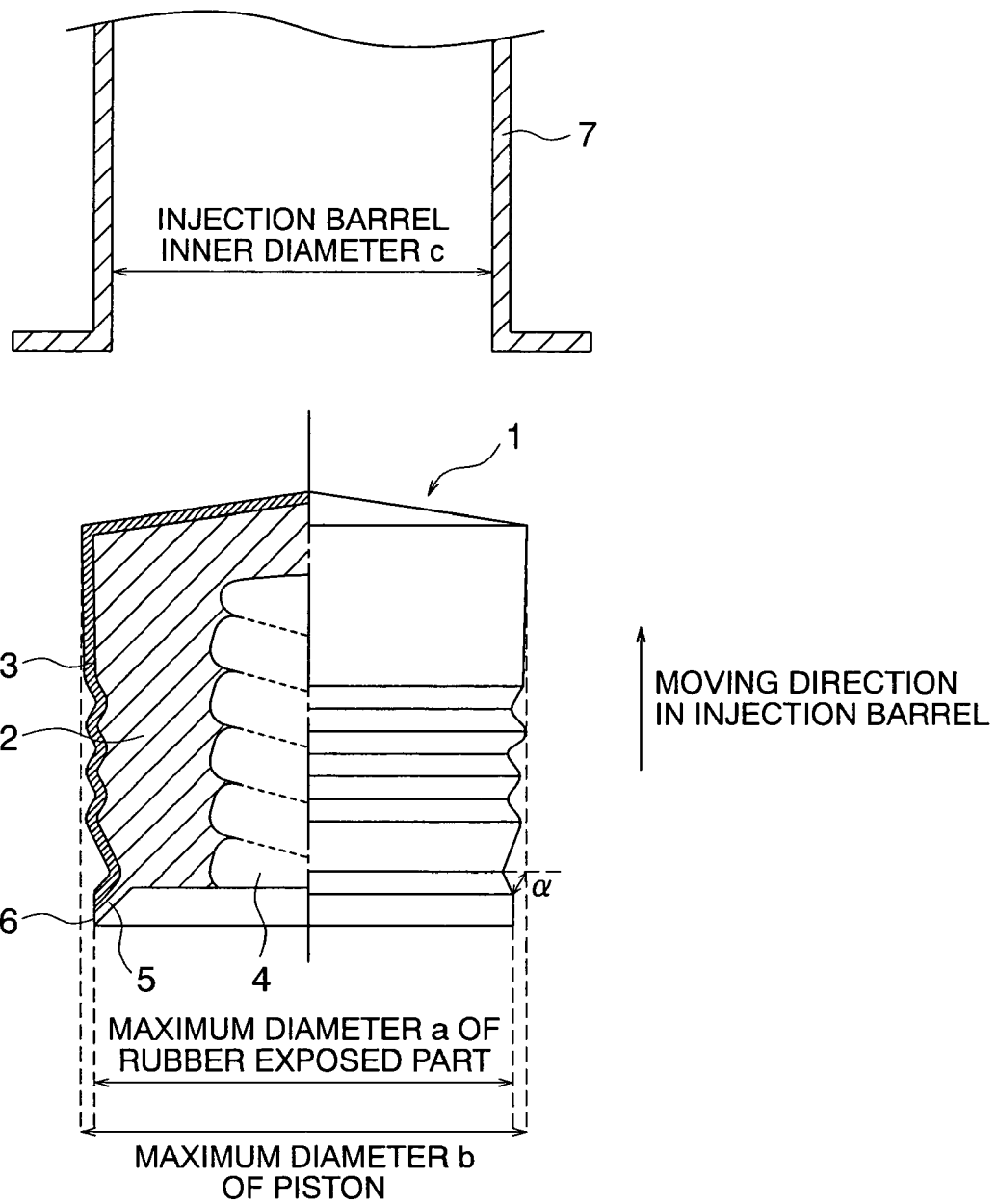
FIG. 2 is a cross-sectional view of another embodiment of a piston for a syringe, in part, according to the present invention, illustrating the dimensions of each part.

We, the inventors, have made various efforts to impart a reuse-preventive mechanism to a prefilled syringe; consequently, we have found that a reuse-preventive device can economically be incorporated in the syringe by designing a stopper for a prefilled syringe with a backstop function. The present invention is based on this finding. The present invention has the following constructive features:

(1) A piston for a syringe for sealing an injection barrel filled with a medicament, comprising a skirt part capable of serving as a backstop device.

(2) The piston for a syringe as described in (1), wherein the piston is subjected to film lamination and/or lubricant coating, the skirt part has a rubber exposed surface forming a contact surface with the injection barrel and at least a part of the rubber exposed surface is inside the maximum outer diameter of the stopper and outside the inner diameter of the injection barrel.

(3) The piston for a syringe as described in (1) or (2), wherein an angle of the skirt part is in a range of 30 to 80° based on a standard surface parallel to a direction in which the piston is slidably moved in the injection barrel.

(4) A prefilled syringe comprising an injection barrel filled with a medicament and sealed by a piston, the piston being a piston for a syringe as described in any one of (1) to (3).

FIG. 1 is a schematic cross-sectional view of one embodiment of a piston for a syringe (which will hereinafter be referred to as "piston") and a prefilled syringe using the same according to the present invention. The piston 1 shown in FIG. 1A comprises a rubber-made piston body 2, the surface of which is laminated with a resin film 3. A plunger rod 4 (not shown) is fitted to the piston at a fitting position. In a preparative step for an injection medicament, the end of an injection barrel 7 is sealed by a cap 8 as shown in FIG. 1C, after which an injection medicament 9 is filled and prepared in an injection barrel 7 shown in FIG. 1B and sealed by the piston 1 to provide the prefilled syringe. Ordinarily, a needle part, plunger part and cover parts for each part (all not shown) are added thereto to prepare a finished article.

In FIG. 2, there is shown another embodiment of a piston for a syringe according to the present invention, as enlarged in part and as a front view in part, in which the same remarks as those in connection with FIGS. 1A-1C have the same meaning.

The piston 1 has a skirt part 5 having a backstop function, is usually subjected to film 3 lamination and/or lubricant coating on the surface thereof. It is desirable, in order to allow contact of the skirt part 5 with the inner wall of the injection barrel 7, to provide a rubber exposed surface 6, since friction resistance is increased when a drawing force is applied to the piston 1.

Moreover, it is desirable that at least a part of the above described rubber exposed surface 6 is inside the maximum outer diameter of the piston, and the rubber exposed surface 6 has an outer diameter which is greater than the inner diameter of the injection barrel. In order to ensure the sealing property, the maximum outer diameter b of the piston 1 is ordinarily enlarged so as to be larger than the inner diameter c of the injection barrel 7, and the position of the rubber exposed surface 6 is controlled so that the rubber exposed surface 6 does not strongly contact the injection barrel 7 so that the resistance during compression is not excessive, and so that a backstop action can be achieved when a drawing force is applied.

For example, maximum diameter (a) of the rubber exposed surface 6 is preferably smaller than a maximum outer diameter (b) of the piston 1 and larger than an inner diameter (c) of the injection barrel 7 (i.e., c<a<b), when the central axes of the piston 1 and the skirt part 5 are coaxial. On the other hand, the object of the present invention can be achieved even in a case of similar axial relation of a<c when these central axes are not coaxial or shifted relative to each other, if at least a part of the exposed rubber surface 6 is in contact with an inner surface of the barrel 7 and, at the same time, a diameter a of the rubber exposed surface 6 wound with the skirt part 5 is larger than the inner diameter c of the injection barrel 7, i.e., a'>c.

Furthermore, the skirt part 5 has preferably an angle ($\alpha$ in FIG. 2) of the skirt part in a range of preferably 30 to 80°, more preferably 40 to 70° based on a standard surface parallel to a direction that the piston for a syringe is slidably moved in the injection barrel. When the angle $\alpha$ is at least 30°, the width of the skirt part 5 can sufficiently be maintained, and a friction resistance sufficient to backstop the piston 1 can be obtained and the slidable resistance is not more than the allowed value when the piston 1 is advanced in the injection barrel 7. When it is adjusted to at most 80°, on the other hand, the skirt part 5 can well be turned up when the piston 1 is backed away.

The skirt part 5 of the piston 1 shown in FIG. 2 is over the whole circumference of the stopper, but it is not always provided over the whole circumference, but can intermittently be provided.

In addition, the position of the skirt part 5 is not particularly limited, but it is preferable to arrange the skirt part at the end of the plunger side as shown in FIG. 2 from the standpoint of ease of the production.

Figure 3A:
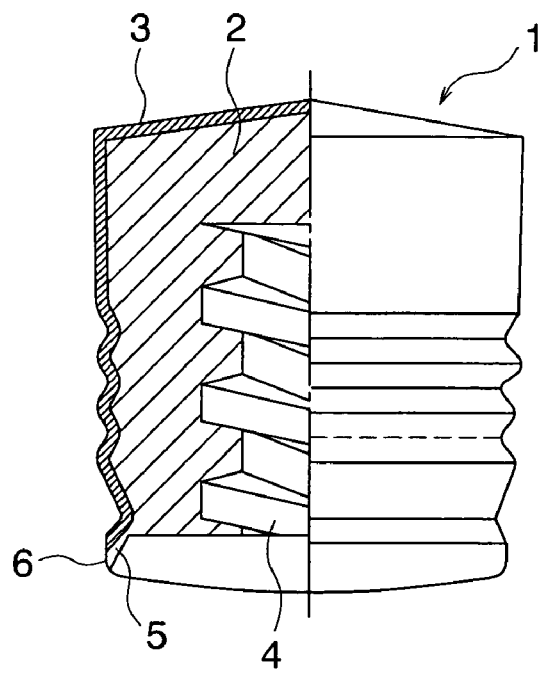
FIGS. 3A-3B are cross-sectional views of further embodiments of a piston for a syringe, in part, according to the present invention, each differing in the shape of the skirt part of the pistons.
Figure 3B:
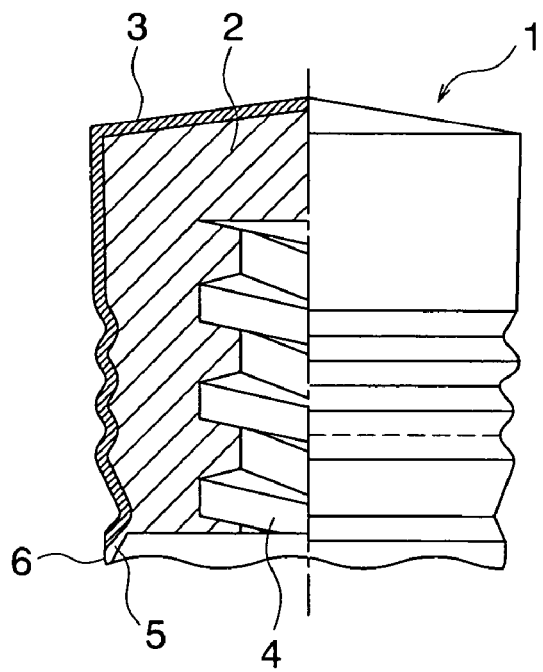
Figure 4A:
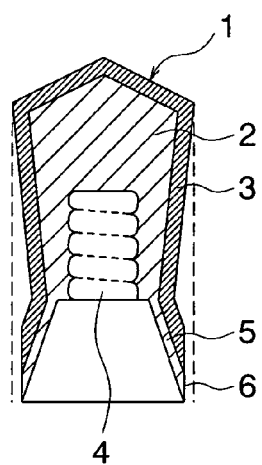
FIGS. 4A-4C are cross-sectional views of still further embodiments of a piston for a syringe according to the present invention, each differing in the shape of the cross-section through the piston.
Figure 4B:
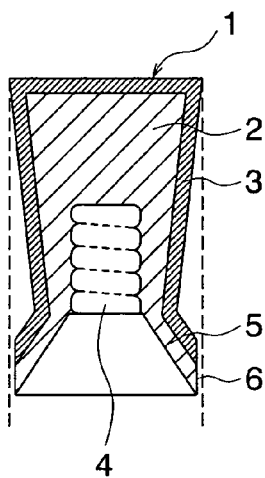
Figure 4C:
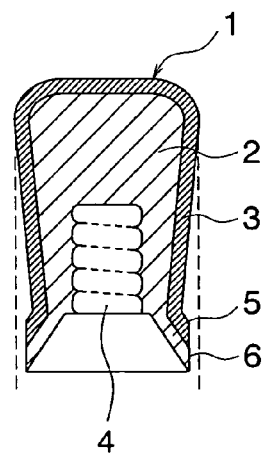

FIGS. 3A and 3B are cross-sectional views of other embodiments of the piston 1 according to the present invention, where the piston 1 has the skirt part 5 in the form of other shapes, and FIGS. 9A to 4C are cross-sectional views of further embodiments of the piston 1 according to the present invention in the form of further shapes, in which the same remarks as those in FIG. 1 and FIG. 2 have the same meanings.

In FIG. 1 to FIG. 4, a case of laminating a rubber-made piston body 2 with a resin film 3 is exemplified, and the laminated resin film 3 is not limited thereto but any material capable of obtaining a required kinematic friction coefficient (e.g. a kinematic friction coefficient of at most 0.2 measured according to JIS K 7218-1986) when fitted to a plunger and pushed into an injection barrel 7 can be used. Accordingly, other known means such as coating of lubricants can be selected for this purpose.

For the resin film 3, fluoro resins can be used such as tetrafluoro ethylene resin (PTFE), tetrafluoroethylene-perfluoroethylene copolymer (PFA), tetrafluoroethylene-hexafluoropropylene copolymer (FEP), tetrafluoroethylene-ethylene copolymer (ETFE), trichlorotrifluoroethylene (PCTFE), poly-vinylidene fluoride (PVDF), polyvinyl fluoride (PVF), etc. and further, ultra-high molecular weight polyethylene, etc. can also be used in addition to the fluoro resins.

Lamination of a rubber-made piston body 2 with a resin film 3 can be carried out by a known prior art technique, for example, a method comprising optionally subjecting one surface of a film to a chemical treatment (chemical etching), sputter etching or corona discharge, arranging it in a shaping mold with a rubber compound to be a basic material for the piston body 1, and then vulcanizing or bonding to form a pre-determined shape. Of course, a site to be laminated includes a part that can be contacted with the inner wall of the injection barrel 7 or with a medicament, etc., without intending to be limited thereto, in addition to at least a part (rubber exposed surface 6) of the contacted surface of the skirt part 5 with the inner wall of the injection barrel 7.

As a lubricant, there can for example be used silicone oils, fluorinated oils, etc. Useful examples of the fluorinated oil are Demnum (commercial name of Daikin Industries, Ltd.), Krytox (commercial name of Du Pont Kabushiki Kaisha), etc. A site to be coated with the lubricant includes a part that can be contacted with the inner wall of the injection barrel 7, etc. without intending to be limited thereto, in addition to at least a part (rubber exposed surface 6) of the contacted surface of the skirt part 5 with the inner wall of the injection barrel 7.

In order to maintain at least a part of the contacted surface of the skirt part 5 with the injection barrel 7 to be the rubber exposed surface 6, for example, there can be employed a method comprising molding rubber in the form of a sheet consisting of a number of rubber-made piston bodies 2 bonded at the skirt part 5, subjecting the resulting sheet to laminate working or lubricant coating and then separating the contacted surface of the skirt part 5 with the injection barrel 7.

The rubber for the material of the rubber-made piston body 2 of the piston is not particularly limited, but can for example be selected from synthetic rubbers or natural rubbers such as butyl rubbers, chlorinated butyl rubbers, isobutylene-isoprene-divinylbenzene-ternary polymerization partially cross-linked butyl rubbers, acrylnitrile-butadiene-rubbers, isoprene rubbers, butadiene rubbers, styrene-butadiene rubbers, ethylene-propyrene rubbers, isoprene-isobutylene rubbers, nitrile rubbers, etc., as a predominant component, to be compounded with fillers, cross-linking agents or the like. As a thermoplastic elastomer, there can also be used solution polymerization type styrene-butadiene rubbers (SBS block copolymer), polyester or polyether urethane rubbers, polyether aromatic polyester block copolymers (polyester rubbers), polyolefin block copolymers, high trans-1,4-polyisoprenes, polyethylenebutyl graft copolymers, syndiotactic polybutadiens and the like.

In addition to the foregoing, relatively soft plastics, for example, plastics of copolymer type and having substantially the same heat resistance (preferably about 130 to 140° C.) as polypropylene, such as polypropylenes of copolymer type, low density polyethylenes, ethylene-vinyl acetate copolymers, etc. can also be used. Moreover, the hardness of the piston of the present invention is not particularly limited, but is suitably selected depending on the shape or the like of the piston and from the standpoint of maintaining the sealing property of a prefilled syringe and compressing the piston with a suitable force as well as effectively exhibiting the backstop function, the hardness is preferably measured by a method defined by JIS K 6253 A, which is preferably within a range of 50 to 65, more preferably 55 to 60.

Regarding the piston of the present invention, in particular, it is eagerly desired to select a material excellent in anti-gas permeability so as to obtain high sanitary properties as well as to stably preserve a solvent for a long time, e.g. three years, in a container (injection barrel). Compounding examples of such a rubber recipe are shown in the following Table 1:

TABLE 1

| Composition | Compounding Example | | | |
|---|---|---|---|---|
| | 1 | 2 | 3 | 4 |
| Butyl Rubber 1) | 100 | | | |
| Chlorinated Butyl Rubber 2) | | 100 | | |
| Isobutylene-Isoprene-Divinylbenzene-Ternary Polymerization Partially Cross-linked Butyl Rubber 3) | | | 100 | |
| Acrylnitrile-Butadiene Rubber 4) | | | | 100 |
| Wet process Hydrous Silica 5) | 35 | 30 | 30 | 20 |
| Dipentanemethylene Thiuram Tetrasulfide 6) | 2.5 | | | |
| Zinc Di-n-dibutylthiocarbamate 7) | 1.5 | | | |
| Active Zinc Oxide 8) | 5 | 4 | 1.5 | |
| Stearic Acid 9) | 1.5 | 3 | | |
| Magnesium Oxide 10) | | 1.5 | | |
| 2-Di-n-Butylamino-4,6-dimercapto-s-triazine 11) | | 1.5 | | |
| 1-1-Bis(t-butylperoxy)-3,3,5-trimethylcyclohexane 12) | | | 2 | 8 |
| Total (by weight) | 145.5 | 140.0 | 133.5 | 128 |
| Vulcanizing Temperature (° C.) | 175 | 180 | 150 | 155 |
| Conditions Time (min) | 10 | 10 | 10 | 10 |

(Note)
1) manufactured by Exxon Chemical Co., Ltd., Esso Butyl #365 (commercial name), bonded isoprene content: 1.5 mol %, Mooney Viscosity; 43 to 51
2) manufactured by Exxon Chemical Co., Ltd., Esso Butyl HT 1066 (commercial name), bonded chlorine content: 1.3 wt %, Mooney Viscosity: 34 to 40
3) manufactured by Bayer AG, Bayer Butyl XL-10000 (commercial name)
4) Nippon Zeon Co., Ltd., Nippol DN 102 (commercial name), bonded acrylonitrile content: 42 wt %, Mooney Viscosity: 60
5) manufactured by Nippon Silica Kogyo Co., Ltd., Nipsil ER (commercial name), pH: 7.5 to 9.0 (5% aqueous solution), filler
6) manufactured by Kawaguchi Kagaku Kogyo Co., Ltd., Accel TRA (commercial name), mp: at least 120° C., vulcanizing agent
7) manufactured by Kawaguchi Kagaku Kogyo Co., Ltd., Accel BZ (commercial name), vulcanizing agent
8) manufactured by Seido Kagaku Kogyo Co., Ltd., Active Zinc White AZO (commercial name), ZnO 93 to 96%, vulcanizing accelerator
9) manufactured by Kao Co., Ltd., Lunac S#30, (commercial name, composition: plant stearic acid), adhesion inhibitor
10) manufactured by Kyowa Kagaku Kogyo Co., Ltd., Kyowa Mag #150 (commercial name), specific surface area: 130 to 170 mg, vulcanizing accelerator
11) manufactured by Sankyo Kasei Co., Ltd., Zisnet DB (commercial name), mp: at least 137° C., vulcanizing agent
12) manufactured by Nippon Yushi Co., Ltd., Perhexa 3M-40 (commercial name), molecular weight: 302, one minute half-life temperature: 149° C., vulcanizing agent The prefilled syringe of the present invention includes any type of prefilled syringes using a piston for the syringe as illustrated above according to the present invention, and the material or shape of the injection barrel part and other parts than the injection barrel, for example, the cap at the front end, injection needle part, plunger rod fitted to the rear end of the piston or the like is not particularly limited. For example, as the material of the injection barrel (-cum-container), plastics are generally used from the viewpoint of the surface roughness, such as cyclic olefinic resins, cyclic olefin-ethylene copolymers, polyethylene terephthalate type resins, polystyrene resins, etc. In particular, it is preferable to selectively use cyclic olefinic resins or cyclic olefin-ethylene copolymers (e.g. used for a sanitary container described in JP-B2-2914826).

The prefilled syringe of the present invention includes any type of syringes that use the sealing stopper as a piston according to the present invention, that is, not only one as shown in FIG. 1(c), but also two compartment type syringes, e.g. as shown in JP-A-8-308688.

ADVANTAGES OF THE INVENTION

Since the sealing stopper or piston for a syringe according to the present invention has a skirt part provided with a back-stop function, compression of the piston can be carried out in an injection barrel, but the withdrawing thereof cannot be carried out. Thus, according to the present invention, reuse can be prevented in an economical and simple manner. That is, a prefilled syringe using the above described sealing stopper or piston can be provided with reuse-preventive function at a low cost, and can prevent the danger of a used syringe being reused after having been thrown away.

What is claimed is:
1. A piston for sealing an injection barrel of a syringe filled with medicament, said piston comprising a skirt part shaped and arranged so as to contact an inner wall of the injection barrel to allow motion of said piston in a direction along a longitudinal axis of the injection barrel, and to restrict movement of said piston in an opposite direction along the longitudinal axis of the injection barrel.
2. The piston as claimed in claim 1, wherein:
said piston is subjected to film lamination and/or lubricant coating;
said skirt part has a rubber exposed surface for contacting the injection barrel;
at least a part of said skirt part is inside a maximum outer diameter of said piston; and
said skirt part has an outer diameter which is greater than an inner diameter of the injection barrel.
3. The piston as claimed in claim 1, wherein an angle of said skirt part is in a range of 30 to 80° measured from a surface that is perpendicular to a direction in which said piston is slidably moved in the injection barrel.
4. A prefilled syringe comprising an injection barrel filled with medicament, and sealed by a piston as claimed in claim 1.
5. The piston as claimed in claim 2, wherein an angle of the skirt part is in a range of 30 to 80° based on a standard surface perpendicular to such a direction that the piston is slidably moved in the injection barrel.
6. A prefilled syringe comprising an injection barrel filled with medicament, and sealed by a piston as claimed in claim 2.
7. A prefilled syringe comprising an injection barrel filled with medicament, and sealed by a piston as claimed in claim 3.
8. A piston for sealing an injection barrel of a syringe filled with medicament, said piston comprising:
a piston body; and
a skirt part extending outwardly from said piston body to contact the injection barrel;

wherein said skirt part is shaped and arranged so as to allow movement of said piston in a direction along a longitudinal axis of the injection barrel, and to effectively prevent movement of said piston in an opposite direction along the longitudinal axis of the injection barrel.

9. The piston as claimed in claim 8, further comprising an outer layer covering a portion of said piston body.

10. The piston as claimed in claim 9, wherein said outer layer comprises a film laminate and/or a lubrication coating.

11. The piston as claimed in claim 8, wherein said piston body comprises rubber, thermoplastic elastomer, or plastic material.

12. The piston as claimed in claim 8, wherein said skirt part extends from said piston body at an angle that ranges from 30 degrees to 80 degrees with respect to a longitudinal axis of said piston body.

13. The piston as claimed in claim 8
wherein said skirt part has an exposed rubber surface for contacting the injection barrel;
wherein at least a part of said skirt part is inside a maximum outer diameter of said piston; and
wherein said skirt part has an outer diameter which is greater than an inner diameter of the injection barrel.

14. The piston as in claim 13, further comprising an outer layer covering a portion of said piston body;
wherein said outer layer comprises a film laminate and/or a lubrication coating;
wherein said piston body is formed of rubber, thermoplastic elastomer, or plastic material;
wherein said skirt part extends from said piston body at an angle that ranges from 30 degrees to 80 degrees with respect to a longitudinal axis of the piston body;
wherein at least a part of said skirt part is inside a maximum outer diameter of said piston; and
wherein said skirt part has an outer diameter which is greater than an inner diameter of the injection barrel.

15. A prefilled syringe comprising an injection barrel filled with medicament, and sealed by a piston as in claim 8.

16. A prefilled syringe comprising an injection barrel filled with medicament, and sealed by a piston as in claim 9.

17. A prefilled syringe comprising an injection barrel filled with medicament, and sealed by a piston as in claim 10.

18. A prefilled syringe comprising an injection barrel filled with medicament, and sealed by a piston as in claim 12.

19. A prefilled syringe comprising an injection barrel filled with medicament, and sealed by a piston as in claim 13.

20. A prefilled syringe comprising an injection barrel filled with medicament, and sealed by a piston as in claim 14.

\* \* \* \* \*